United States Patent
Marass et al.

(10) Patent No.: US 11,759,609 B2
(45) Date of Patent: Sep. 19, 2023

(54) INTRODUCER POSITIONING DEVICE FOR CONTROLLING A CATHETER SHAFT

(71) Applicant: St. Jude Medical, Cardiology Division, Inc., St. Paul, MN (US)

(72) Inventors: Tim Marass, Minneapolis, MN (US); David Kim, Plymouth, MN (US); Ryan Hendrickson, Albertville, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 523 days.

(21) Appl. No.: 16/959,476

(22) PCT Filed: Jan. 7, 2019

(86) PCT No.: PCT/US2019/012498
§ 371 (c)(1),
(2) Date: Jul. 1, 2020

(87) PCT Pub. No.: WO2019/136357
PCT Pub. Date: Jul. 11, 2019

(65) Prior Publication Data
US 2021/0069473 A1  Mar. 11, 2021

Related U.S. Application Data

(60) Provisional application No. 62/614,520, filed on Jan. 8, 2018.

(51) Int. Cl.
*A61M 25/01* (2006.01)
*A61B 18/14* (2006.01)
(Continued)

(52) U.S. Cl.
CPC ..... *A61M 25/0136* (2013.01); *A61B 18/1492* (2013.01); *A61B 2018/00345* (2013.01);
(Continued)

(58) Field of Classification Search
CPC ...... A61M 25/0136; A61M 2025/0006; A61M 2025/0008; A61M 2205/3507;
(Continued)

(56) References Cited

U.S. PATENT DOCUMENTS

2006/0079859 A1* 4/2006 Elkins ............... A61M 25/0074
604/284
2014/0275991 A1  9/2014 Potter et al.
(Continued)

FOREIGN PATENT DOCUMENTS

AU  2013200536 B2  2/2013
AU  2015200135 B2  2/2015

*Primary Examiner* — Amber R Stiles
*Assistant Examiner* — Nelson Louis Alvarado, Jr.
(74) *Attorney, Agent, or Firm* — Armstrong Teasdale LLP

(57) ABSTRACT

The present disclosure generally relates to medical devices and methods for navigating a catheter shaft into the body of a subject during an intracoronary or other medical procedure and controlling the distal end of the catheter shaft. The present disclosure includes the use of an introducer positioning device that may be used in combination with an introducer. The introducer positioning device when used in combination with an introducer allows a catheter shaft to be inserted therethrough and into the introducer shaft located in the introducer where a distal end of the catheter shaft is aligned with the distal end of the introducer shaft.

20 Claims, 7 Drawing Sheets

(51) Int. Cl.
 *A61B 18/00* (2006.01)
 *A61M 25/00* (2006.01)
(52) U.S. Cl.
 CPC .............. *A61B 2018/00577* (2013.01); *A61M 2025/0006* (2013.01); *A61M 2025/0008* (2013.01); *A61M 2205/3507* (2013.01)
(58) Field of Classification Search
 CPC ...... A61M 2205/3523; A61M 25/0662; A61M 25/0113; A61M 25/01; A61M 25/0133; A61M 2025/0681; A61B 18/1492; A61B 2018/00345; A61B 2018/00577; A61B 2090/061; A61B 2090/062; A61B 2090/0811
 See application file for complete search history.

(56) References Cited

U.S. PATENT DOCUMENTS

| | | |
|---|---|---|
| 2014/0378970 A1 | 12/2014 | Thomspon |
| 2015/0141914 A1* | 5/2015 | Fasano ............... A61M 25/0113 604/95.01 |
| 2022/0322969 A1* | 10/2022 | Korotko ................ A61M 25/00 |

* cited by examiner

INTRODUCER POSITIONING DEVICE FOR CONTROLLING A CATHETER SHAFT

CROSS REFERENCE TO RELATED APPLICATIONS

This application is the national stage entry of PCT/US2019/012498, filed on Jan. 7, 2019, which claims the benefit of priority to U.S. provisional application Ser. No. 62/614,520, filed Jan. 8, 2018, both of which are incorporated herein by reference in their entirety.

A. FIELD OF THE DISCLOSURE

The present disclosure relates generally to navigating medical devices including catheter shafts. In particular, in many embodiments, the present disclosure relates to an introducer positioning device and related methods of use for navigating the distal end of a catheter shaft through the vasculature towards a target organ, such as the heart, in the body of a subject while controlling its position for improved safety and efficacy. The introducer positioning devices described herein may be a separate medical device, or may be an integral part of another medical positioning device used for steering a catheter shaft to a desired location.

B. BACKGROUND

Interventional cardiology works with numerous types of guidewires, sheaths and catheters for providing cardiac assessment and therapy. For example, electrophysiology catheters are used in a variety of diagnostic, therapeutic, and/or mapping and ablative cardiology procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death. Balloon catheters are also widely used in interventional cardiology for numerous treatments.

Typically, a catheter or catheter sheath is deployed and manipulated through a patient's vasculature to the intended site, for example, a site within a patient's heart. In many cases, the catheter or catheter sheath is used in combination with a leading guidewire so as to allow easier and safer access to the intended site. The guidewire may first be introduced into the vasculature to the intended site and then the catheter threaded over the guidewire to the site. In order to improve the overall procedure and outcome, it is desirable for an operator to know the position and orientation of the catheter, and specifically the tip of the catheter, and then to visualize the guidewire as it is navigated within the body of the patient in order to minimize physical injury to the tissues surrounding the desired organ and ensure that the guidewire reaches its intended target. Some general methods for determining the position and orientation of medical devices using fluoropaque markers such as a metallic coil and/or an active impedance-sensing electrode are known in the art. Improving these known devices and methods may provide improved reliability and patient outcomes.

BRIEF SUMMARY OF THE DISCLOSURE

The present disclosure generally relates to medical devices and methods for navigating a catheter shaft into the body of a subject or patient during an intracoronary or other medical procedure and closely controlling the distal end of the catheter shaft, which may be an ablation catheter shaft, for example. In many embodiments, the present disclosure includes the use of an introducer positioning device that may be used in combination with a steerable introducer including a handle for steering the introducer through the vasculature of a subject. The introducer positioning device, when used in combination with an introducer, allows a catheter shaft to be inserted therethrough and into a lumen of the introducer shaft connected to the introducer where a distal end of the catheter shaft is aligned with the distal end of the introducer shaft. Once the alignment of the distal ends has been completed, a mechanism or other component on the exterior of the introducer positioning device is engaged that clamps onto or otherwise locks the portion of the catheter shaft located in the introducer positioning device thus limiting any further movement. In many embodiments, the clamping mechanism is connected to, or integral with, an adjustable slider or adjustable rotating member that can be used to advance the catheter shaft out of the introducer positioning device upon engagement after locking. Once the clamping/locking of the catheter shaft is complete, the adjustable slider or adjustable rotating member is used to advance the catheter shaft out of the introducer shaft by a known amount, which may be indicated on the exterior of the introducer positioning device. As such, the user of the medical device will know the exact position of the distal end of the catheter shaft by knowing the amount that the catheter shaft has been advanced by the adjustable slider or adjustable rotating knob outside of the introducer shaft. The present disclosure further relates to methods of controlling the distal end of a catheter shaft inside of a body as well as kits and systems including the introducer positioning device.

In one embodiment, the present disclosure is directed to an introducer positioning device for controlling the position of a distal end of a catheter shaft. The introducer positioning device comprises: (i) a securement component for securing the introducer positioning device to a medical device; (ii) an entry port configured to receive the catheter shaft; and (iii) a mechanism for clamping to the catheter shaft and for advancing and measuring catheter shaft travel through the introducer positioning device.

In another embodiment, the present disclosure is directed to a steerable medical device for introducing a catheter shaft into a subject during a procedure. The steerable medical device comprises: (i) a handle comprising a steerable introducer shaft including a lumen and a means for steering the steerable introducer shaft; and (ii) an introducer positioning device coupled to the handle and comprising an entry port for a catheter shaft having a distal end, a means for clamping the catheter shaft having a distal end, and a means for advancing and measuring one or more lengths of the catheter shaft through the introducer positioning device and into the lumen of the introducer shaft; wherein the means for advancing and measuring one or more lengths of the catheter shaft is connected to the means for clamping the catheter shaft.

In another embodiment, the present disclosure is directed to a method of tracking a distal end of a catheter shaft inside the body of a subject. The method comprises: (i) advancing the catheter shaft through an introducer positioning device and into a lumen of a steerable introducer shaft; (ii) aligning the distal end of the catheter shaft with a distal end of the steerable introducer shaft; (iii) engaging a means for clamping the catheter shaft located in the introducer positioning device such that the catheter shaft is locked into place by the means for clamping; (iv) introducing the catheter shaft and steerable introducer shaft to a desired location in a subject; and (v) engaging a means for advancing the catheter shaft and advancing and measuring a length of the catheter shaft through the introducer positioning device and steerable introducer shaft such that the distal end of the catheter shaft extends past the distal end of the introducer shaft.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
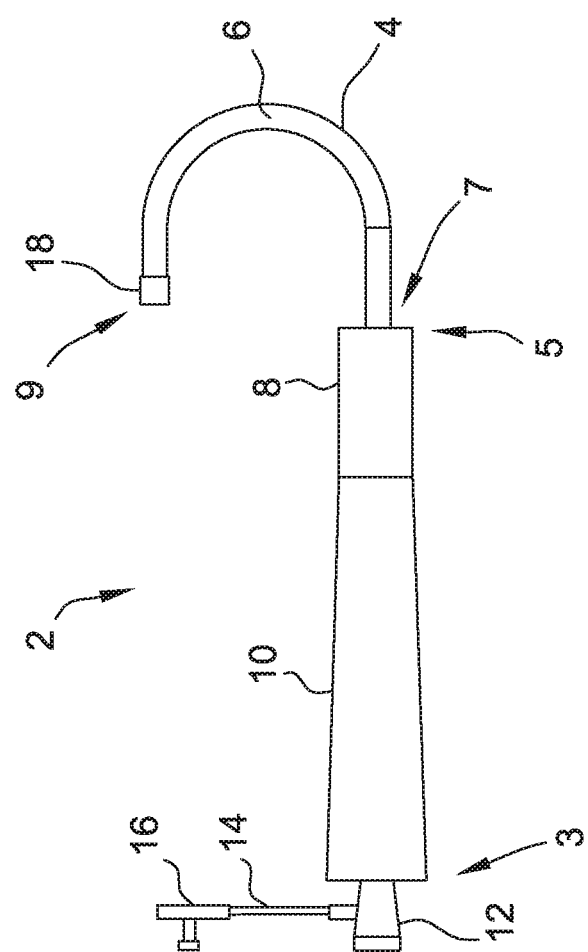
FIG. 1 illustrates a conventional introducer suitable for use with the introducer positioning devices of the present disclosure.

The present disclosure provides medical devices for directing catheter shafts and the like in the human vasculature for known medical purposes. The medical devices of the present invention allow for a user to closely control, monitor, and understand the position of the distal end of a catheter (also referred to as a "catheter tip"), such as an ablation catheter, within the human vasculature. By using an introducer positioning device as described herein, a user can first introduce a catheter shaft through an entry port configured to receive the catheter shaft and into the introducer positioning device and then into the lumen of an introducer shaft attached to an introducer to align the distal end of the catheter shaft with the distal end of the introducer shaft. Once the alignment of the two distal ends is completed, a mechanism on the introducer positioning device may be engaged or activated to lock the catheter shaft in place relative to the introducer shaft such that any subsequent movement of the distal end of the catheter shaft can be closely controlled and measured by the introducer positioning device. As such, during a procedure and after the introducer has been used to navigate the introducer shaft and catheter shaft to a desired location in the vasculature, an operator can advance the distal end of the catheter shaft out of the introducer shaft a known amount using a sliding or rotational mechanism located on the exterior of the introducer positioning device resulting in the user knowing the exact position of the distal end of the catheter shaft relative to the distal end of the introducer shaft. In many embodiments described herein, the introducer positioning device will include measurement markings on the exterior thereof to show the exact distance that the distal end of the catheter has been extended out of the introducer shaft.

Additionally the medical devices of the present invention can securely maintain the position of the distal end of a catheter shaft relative to an introducer during a procedure through the locking action mentioned above. This is important in many procedures, including ablation procedures where it is highly desirable that the catheter shaft be positioned securely in the delivery catheter to maintain a consistent force during a procedure. The disclosed embodiments may lead to more consistent and improved patient outcomes.

For purposes of this description, the introducer positioning devices of the present disclosure will generally be described in many embodiments as a standalone medical device that may be coupled to one or more medical devices prior to use in a procedure. For example, the introducer positioning devices as described herein may be coupled to an introducer, such as an Agilis™ NxT Steerable Introducer (St. Jude Medical), prior to a procedure such that the introducer positioning devices acts as a link between a catheter and the introducer. It is contemplated, however, that the introducer positioning devices and features thereof of the present disclosure may be equally suitable for incorporation directly into the handle of an introducer to produce an introducer made specifically for working with non-steerable catheters. It is further contemplated that the introducer positioning devices and features thereof of the present disclosure may be equally suitable for integration directly into a non-steerable catheter that could then be mated to a device such as an Agilis™ NxT Steerable Introducer (St. Jude Medical), or another introducer or steerable medical device. The introducer positioning devices of the present disclosure may be single use medical devices, or may be multiple-use, re-sterilizable medical devices. The introducer positioning devices and their uses are described in further detail hereinbelow.

As noted herein, the described introducer positioning device in many embodiments of the present disclosure may be used in combination with a conventional uni-directional or bi-directional introducer that includes an introducer shaft having a lumen therein. The introducer shaft having a lumen therein is capable of accepting a catheter shaft therein for use during a procedure. Generally, the introducer positioning device is first attached to, and engaged with, the introducer using a securement component to provide a unitary medical device. The securement component may include a locking mechanism or locking handle that swivels, as described below, in some embodiments. Once the unitary device is formed, the distal end of a catheter shaft may be introduced into an entry port on the introducer positioning device and through the introducer positioning device and into the lumen of the introducer shaft, which is connected to the steerable introducer. The catheter shaft may be attached to a catheter handle (steerable or non-steerable) to facilitate the introduction of the catheter shaft into and through the introducer positioning device.

Once the distal end of the catheter shaft has been introduced into the introducer shaft, the distal end of the catheter shaft is aligned with the distal end of the introducer shaft; that is, the distal end of the catheter shaft is fed through the introducer shaft until the distal ends are in alignment. In many embodiments, the distal end of the introducer shaft will include one or more radiopaque markers to illuminate the distal end of the introducer shaft under fluorescence that is commonly used in vasculature procedures.

Once the distal ends are aligned, a mechanism or actuator is engaged on the exterior of the introducer positioning device that results in a clamping of the catheter shaft present inside of the introducer positioning device such that it is crimped and/or locked into place. This mechanism, which may include one or more connected or non-connected parts or components, generally includes a means for clamping to the catheter shaft and locking it into place and means for advancing and measuring catheter shaft travel within the introducer positioning device as described herein. The mechanism on the exterior of the introducer positioning device may be any suitable single or multiple piece or component mechanism including a sliding mechanism (i.e., an adjustable slider), for example, that includes a clamping or crimping means for locking the catheter shaft in place. Alternatively, the mechanism on the exterior may be a single or multiple piece or component rotational mechanism that includes a clamping or crimping means for locking the catheter shaft in place. The clamping or crimping means of the mechanism of the introducer positioning devices may be fabricated to be compatible with a large number of catheter French sizes to accommodate a wide range of catheter shafts. In some embodiments, the clamping or crimping means of the mechanism may include a first member and a second member sized and configured to sandwich the catheter shaft therebetween. The clamping or crimping means may be formed from any of a number of high friction materials conventionally known in the art (e.g., materials having a static coefficient of friction of approximately 0.4 or greater). In some desirable embodiments, the clamping or crimping means may be formed from a silicone-based material.

After the mechanism or actuator of the introducer positioning device has been engaged and the catheter shaft is locked inside of the introducer positioning device, an operator may introduce the introducer shaft (and the catheter shaft contained therein) into the vasculature of a subject and navigate and steer the distal end of the introducer shaft to a desired location with the subject. Once the desired destination within the subject has been reached, the operator may then use the mechanism (e.g., the sliding mechanism or the rotational mechanism) or another component to advance the distal end of the catheter shaft out of the introducer shaft a known amount, which may be indicated on the exterior of the introducer positioning device; that is, the distal end of the catheter shaft, which may contain one or more ablation electrodes in some embodiments, may be advanced out of the introducer shaft by a known length such that the operator will know exactly how far from the distal end of the introducer shaft the distal end of the catheter shaft is located. This distance may be shown in numerical (or other) markings on the exterior of the introducer positioning device. Alternatively, this distance may be measured and shown electronically via a screen on the exterior of the introducer positioning device. In other embodiments, this measurement may be transmitted, via wire or wirelessly, to a screen or other instrument for viewing. As such, the introducer positioning devices allow a user to know almost the exact location of the tip of the catheter shaft during a procedure, which may result in improved patient outcomes. Once the desired procedure is complete, the distal portion of the catheter shaft that had been extended out of the distal end of the introducer shaft may be recalled back into the introducer shaft using the sliding mechanism and the introducer shaft removed from the individual.

Referring now to the drawings, and specifically to FIG. 1, there is shown an introducer 2 suitable for use in combination with the introducer positioning devices described herein. Although the introducer positioning devices of the present disclosure are generally described herein in combination with an introducer as shown generally in FIG. 1, it is within the scope of the present disclosure to use other types and configurations of introducers or similar steerable medical devices in combination with the introducer positioning devices. Introducer 2 may be used to provide stability for a catheter (not shown in FIG. 1) during the catheter access and positioning. Introducer 2 has proximal end 3 and distal end 5 and includes introducer shaft 4 having proximal end 7, distal end 9 and lumen 6, rotational knob 8 for steering introducer shaft 4 within a human vasculature (not shown in FIG. 1), and introducer handle 10. Introducer 2 further includes hemostasis hub 12 and sideport tubing 14 including stopcock 16. Introducer 2 further includes radiopaque tip marker 18 to enhance fluorescence visibility during an intravascular procedure. Introducer 2 may be a unidirectional or a bi-directional introducer.

Figure 2:
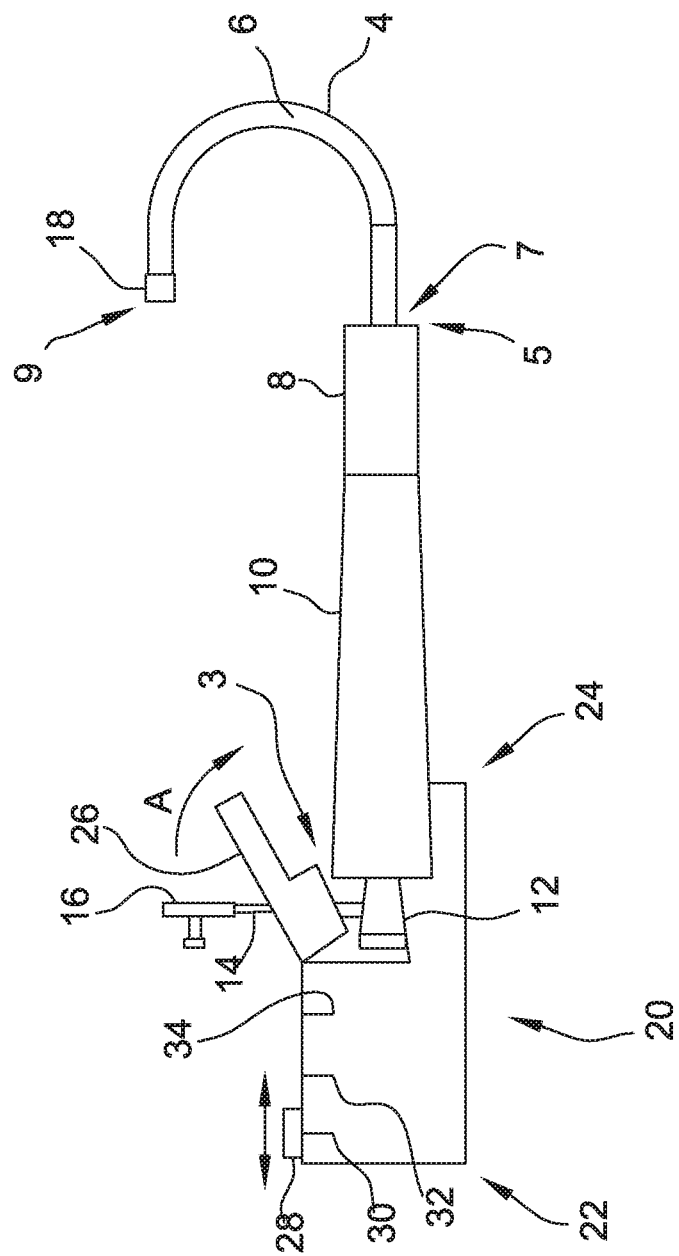
FIG. 2 illustrates the introducer of FIG. 1 further including an introducer positioning device connected to proximal end of the introducer.

Referring now to FIG. 2, there is shown introducer 2 of FIG. 1 further including an introducer positioning device 20 of the present disclosure connected to and engaged with proximal end 3 of introducer 2. Introducer positioning device 20 has proximal end 22 and distal end 24 and includes locking handle 26 that swivels in the direction of arrow A to lock introducer 2 into introducer positioning device 20. Introducer positioning device 20 further includes sliding mechanism 28 that slides along arrow B to advance a locked catheter shaft (not shown in FIG. 2 but see FIG. 5) as further discussed herein. Sliding mechanism 28 is attached to a clamping mechanism (not shown in FIG. 2 but see FIG. 3) to facilitate the clamping and locking of a catheter shaft (not shown in FIG. 2 but see FIG. 3) as further discussed herein. In many embodiments, measurement markers 30, 32, and 34 may designate lengths in millimeter increments. Introducer positioning device 20 further includes measurement markers 30, 32, and 34 for determining the amount of movement of a catheter shaft through introducer positioning device 20 as further discussed herein. Introducer positioning device 20 further includes an access port (not shown in FIG. 2 but see FIG. 3) on proximal end 22 for allowing a catheter shaft (not shown in FIG. 2) to enter introducer positioning device 20 as further discussed herein.

Figure 3:
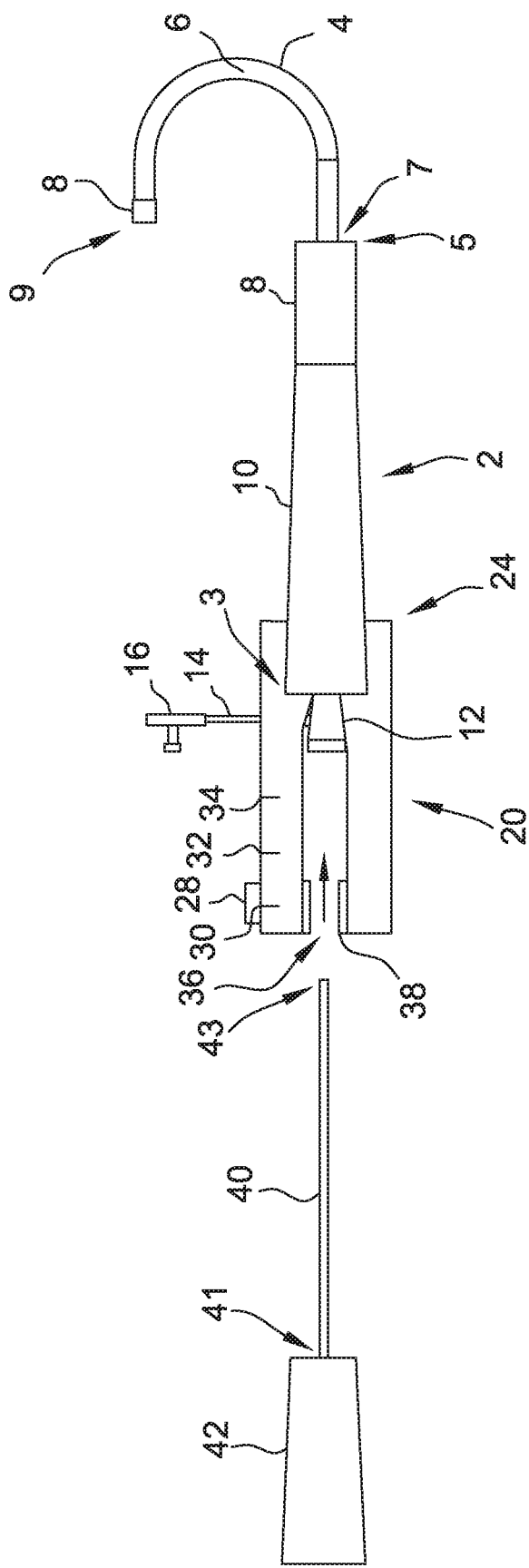
FIG. 3 illustrates the introducer positioning device of FIG. 2 fully engaged with the introducer.

Referring now to FIG. 3, there is shown the introducer positioning device 20 of FIG. 2 fully engaged with introducer 2. FIG. 3 further illustrates introducer positioning device 20 as including access port 36 and clamping mechanism 38. Clamping mechanism 38 connected to, and is engaged by, sliding mechanism 28. FIG. 3 also shows catheter shaft 40 having proximal end 41 and distal end 43 attached to catheter handle 42. Catheter shaft 40 may be inserted into access port 36 of introducer positioning device 20 as further described herein.

Figure 4:
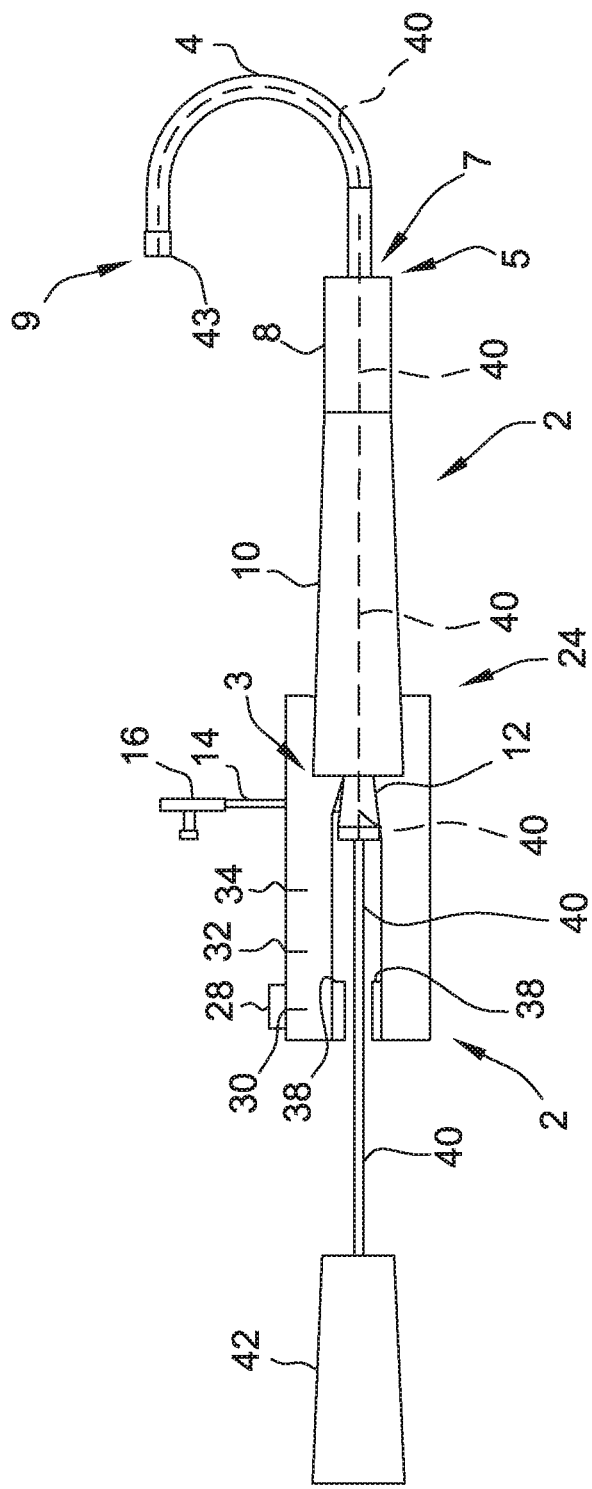
FIG. 4 illustrates a catheter shaft located in an introducer positioning device, an introducer, and an introducer shaft.

Referring now to FIG. 4, there is shown catheter shaft 40 located in introducer positioning device 20, introducer 2, and introducer shaft 4. Catheter shaft 40 has been introduced into introducer positioning device 20 via access port 36 and into introducer 2 via hemostasis hub 12. Distal end 9 of introducer shaft 4 is aligned with distal end 43 of catheter shaft 40.

Figure 5:
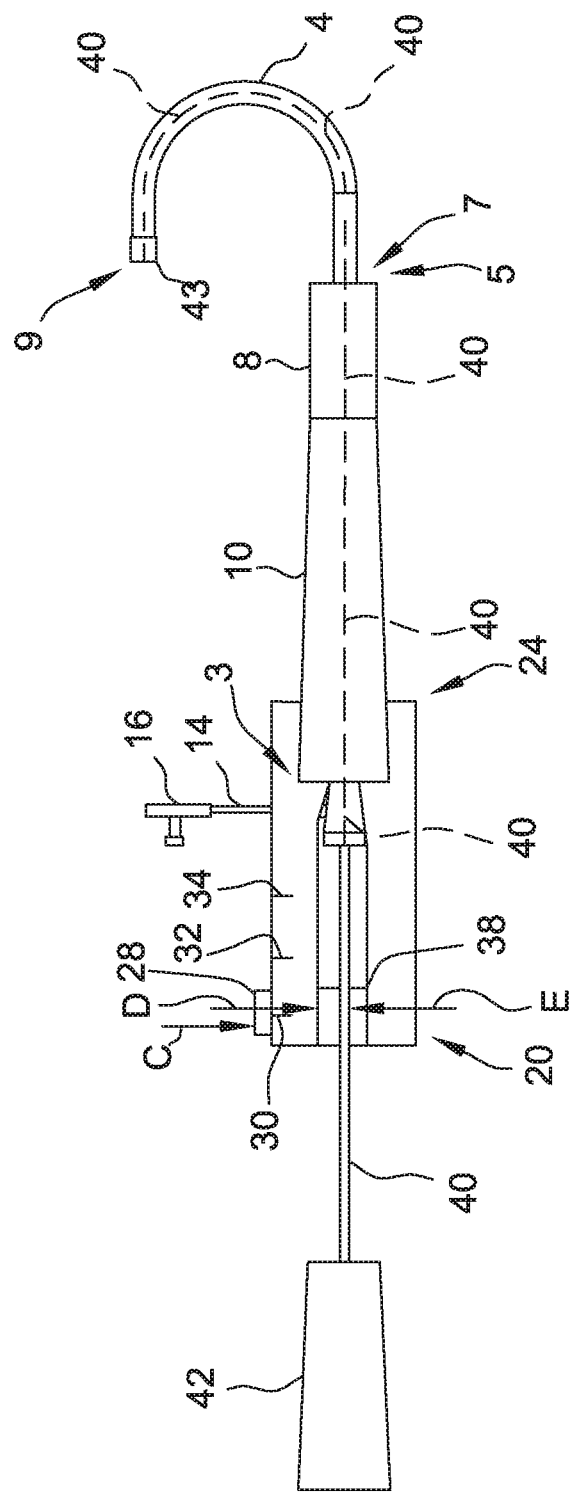
FIG. 5 illustrates a catheter shaft locked in place in an introducer positioning device via a clamping mechanism which has been engaged by a sliding mechanism.

As noted above, once the distal ends of the catheter shaft and the introducer shaft have been aligned as shown in FIG. 4, the clamping mechanism of the introducer positioning device is engaged to secure or lock the catheter shaft in place in the introducer positioning device. This locking/clamping of the catheter shaft allows the introducer positioning device to be able to control any movement of the catheter shaft. Referring now to FIG. 5, there is shown catheter shaft 40 locked in place in introducer positioning device 20 via clamping mechanism 38 which has been engaged by sliding mechanism 28. Sliding mechanism 28 engages clamping mechanism 38 when sliding mechanism is engaged along arrow C, which in turn causes clamping mechanism 38 to move along arrows D and E to secure or lock catheter shaft 40 in place with introducer positioning device 20.

Once the distal ends have been aligned and catheter shaft has been secured inside of the introducer positioning device as described herein, an operator may guide the introducer shaft (and hence the catheter shaft located within the introducer shaft) to a desired location within the vasculature of a subject. Once the desired destination is reached, the operator may then use the sliding mechanism to advance the distal end of the catheter shaft a known distance out of the distal end of the introducer shaft; that is, the sliding mechanism is used to advance the distal end of the catheter shaft out of the distal end of the introducer shaft, which remains stationary. The amount that the distal end of the catheter shaft is advanced may be indicated on the exterior of the introducer positioning device using one or more measurement markers. In practice this allows the operator to precisely position the distal end of the catheter at a desired location, such as next to a lesion or other point of interest.

Figure 6:
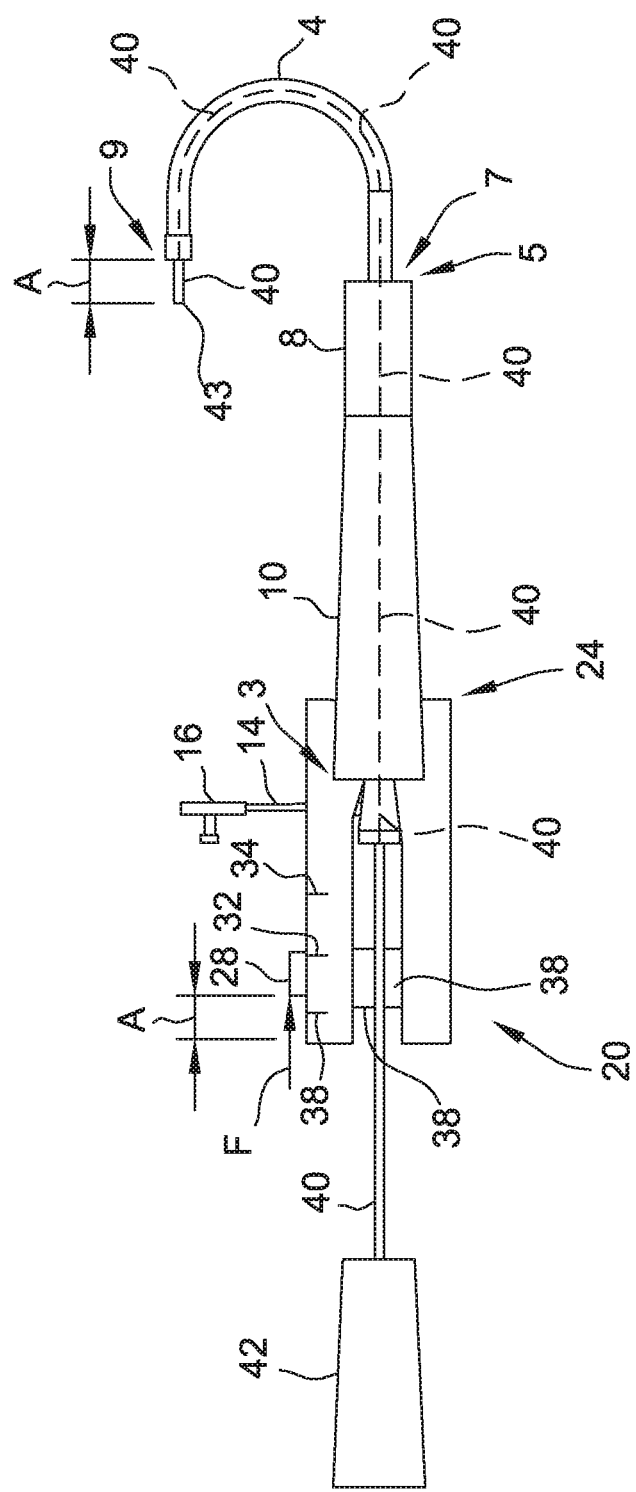
FIG. 6 illustrates a catheter shaft locked in place in an introducer positioning device via a clamping mechanism which has been engaged by a sliding mechanism.

Referring now to FIG. 6, there is shown distal end 43 of catheter shaft 40 advanced out of distal end 9 of introducer shaft 6 by the same amount A that sliding mechanism 28 has moved along arrow F. As sliding mechanism 28 moves along arrow F, catheter shaft 40 is advanced through introducer positioning device 20, through introducer 2 and introducer shaft 6 and out of distal end 9 of introducer shaft 6 by the same amount that sliding mechanism 28 is moved. In operation, a user may easily use measurement markers 30, 32, and 34 to determine the exact length that distal end 43 of catheter shaft 40 has been moved out of distal end 9 of introducer shaft 6.

In use, once catheter shaft 40 has been used for its intended purpose (an ablation procedure, for example), distal end 43 of catheter shaft 40 can be retrieved back into distal end 9 of introducer shaft 6 by moving sliding mechanism 28 back to its original position. The operator may then complete the procedure by withdrawing introducer shaft 6 from the body.

Other embodiments of the present disclosure include methods of using the introducer positioning device as described herein, as well kits or systems including the introducer positioning device with one or more other medical devices, such as an introducer, a catheter, and the like. In one specific embodiment, a kit is disclosed that includes an introducer positioning device as described herein bundled together with a steerable introducer. In another specific embodiment, a kit is disclosed that includes a non-steerable catheter bundled with a steerable introducer and an introducer positioning device. In another specific embodiment, a method of tracking a distal end of a catheter shaft inside the body of a subject is disclosed. The method comprises: (i) advancing the catheter shaft through an introducer positioning device and into a lumen of a steerable introducer shaft; (ii) aligning the distal end of the catheter shaft with a distal end of the steerable introducer shaft; (iii) engaging a means for clamping the catheter shaft located in the introducer positioning device such that the catheter shaft is locked into place by the means for clamping; (iv) introducing the catheter shaft and steerable introducer shaft to a desired location in a subject; and (v) engaging a means for advancing the catheter shaft and advancing and measuring a length of the catheter shaft through the introducer positioning device and steerable introducer shaft such that the distal end of the catheter shaft extends past the distal end of the introducer shaft.

Figure 7:
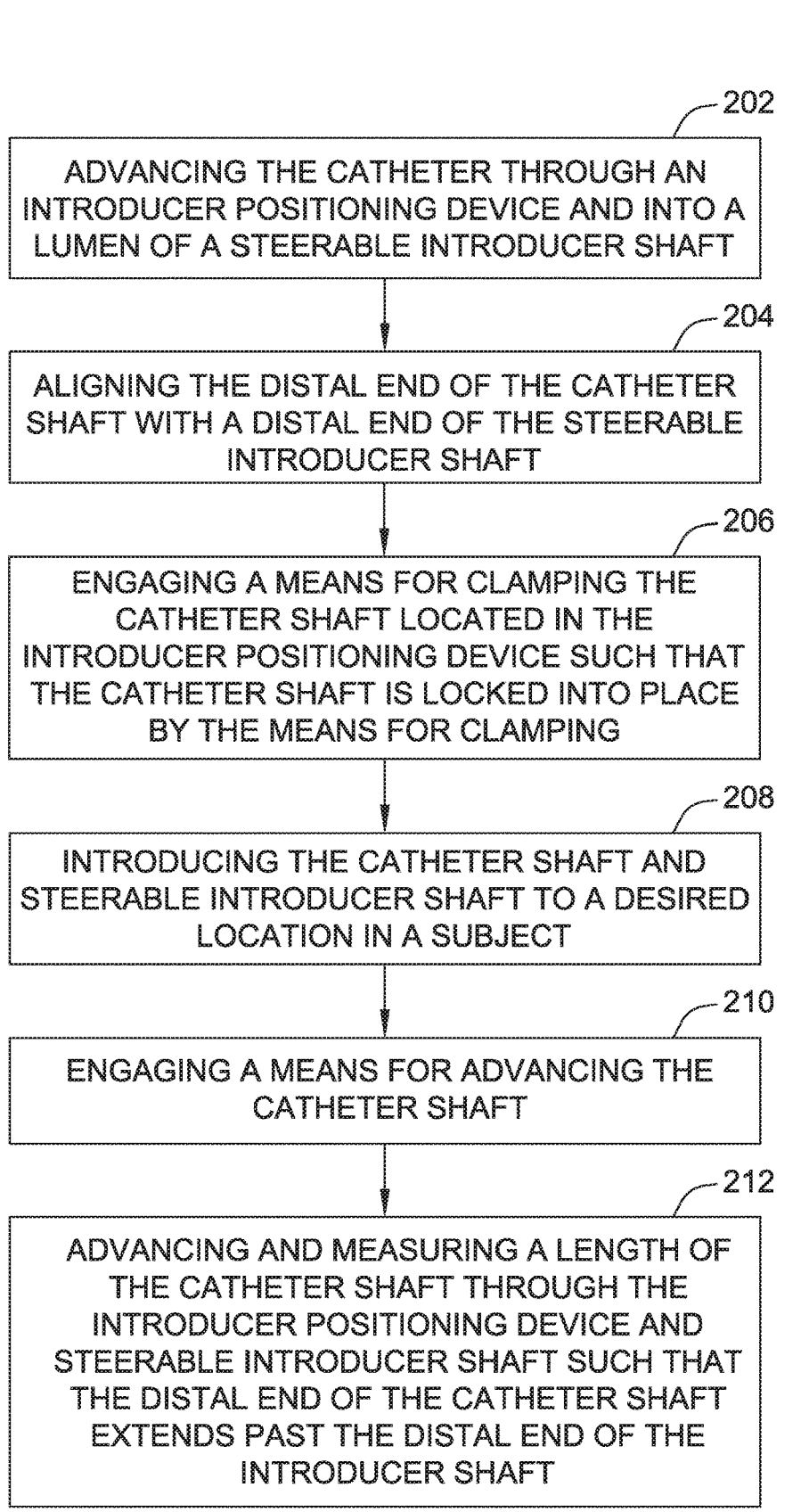
FIG. 7 is a flow diagram of a method of controlling a distal end of a catheter shaft inside the body of a subject.

FIG. 7 is a flow diagram of a method 200 of controlling a distal end of a catheter shaft inside the body of a subject. Method 200 includes advancing 202 the catheter shaft through an introducer positioning device and into a lumen of a steerable introducer shaft and aligning 204 the distal end of the catheter shaft with a distal end of the steerable introducer shaft. Method 200 further includes engaging 206 a means for clamping the catheter shaft located in the introducer positioning device such that the catheter shaft is locked into place by the means for clamping and introducing 208 the catheter shaft and steerable introducer shaft to a desired location in a subject. Method 200 further includes engaging 210 a means for advancing the catheter shaft and advancing 212 and measuring a length of the catheter shaft through the introducer positioning device and steerable introducer shaft such that the distal end of the catheter shaft extends past the distal end of the introducer shaft.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An introducer positioning device for controlling a position of a distal end of a catheter shaft, the introducer positioning device comprising:
   a securement component for securing the introducer positioning device to a medical device;
   an entry port configured to receive the catheter shaft;
   a mechanism for clamping to the catheter shaft and for advancing and measuring catheter shaft travel through the introducer positioning device while the catheter shaft is clamped.

2. The introducer positioning device of claim 1, wherein the mechanism includes a linear sliding component for advancing and measuring catheter shaft travel through the introducer positioning device.

3. The introducer positioning device of claim 1, wherein the mechanism includes a rotational component for advancing and measuring catheter shaft travel through the introducer positioning device.

4. The introducer positioning device of claim 3, wherein the rotational component is a twist knob or a wheel.

5. The introducer positioning device of claim 1, wherein the mechanism includes a first member and a second member sized and configured to sandwich the catheter shaft therebetween.

6. The introducer positioning device of claim 5, wherein the first member and the second member are formed from a high friction material.

7. The introducer positioning device of claim 6, wherein the high friction material is a silicone-based material.

8. The introducer positioning device of claim 1, wherein the mechanism includes visual length markers.

9. The introducer positioning device of claim 1, further including a component for wirelessly transferring measuring data to another device.

10. A steerable medical device for introducing a catheter shaft into a subject during a procedure, the steerable medical device comprising:
    a handle comprising:
    a steerable introducer shaft including a lumen; and
    a means for steering the steerable introducer shaft;
    an introducer positioning device coupled to the handle and comprising:
    an entry port for a catheter shaft having a distal end;
    a means for clamping the catheter shaft having a distal end; and
    a means for advancing and measuring one or more lengths of the catheter shaft through the introducer positioning device and into the lumen of the steerable introducer shaft while the catheter shaft is clamped; wherein the means for advancing and measuring one or more lengths of the catheter shaft is connected to the means for clamping the catheter shaft.

11. The steerable medical device of claim 10, wherein the handle additionally comprises a hemostasis hub.

12. The steerable medical device of claim 10, wherein the means for advancing and measuring one or more lengths of the catheter shaft includes a linear sliding mechanism.

13. The steerable medical device of claim 10, wherein the means for advancing and measuring one or more lengths of the catheter shaft includes a rotational mechanism.

14. The steerable medical device of claim 13, wherein the rotational mechanism is a twist knob or a wheel.

15. The steerable medical device of claim 10, wherein the means for clamping the catheter shaft having a distal end includes a first member and a second member sized and configured to sandwich the catheter shaft having a distal end therebetween.

16. The steerable medical device of claim 10, wherein the means for clamping the catheter shaft having a distal end is formed from a high friction material.

17. The steerable medical device of claim 16, wherein the high friction material is a silicone-based material.

18. The steerable medical device of claim 10, wherein the means for advancing and measuring one or more lengths of the catheter shaft through the introducer positioning device includes visual length markers.

19. The steerable medical device of claim 10, further including a means for wirelessly transferring measuring data to another device.

20. A method of tracking a distal end of a catheter shaft inside a body of a subject, the method comprising:
    advancing the catheter shaft through an introducer positioning device and into a lumen of a steerable introducer shaft;
    aligning the distal end of the catheter shaft with a distal end of the steerable introducer shaft;
    engaging a means for clamping the catheter shaft located in the introducer positioning device such that the catheter shaft is locked into place by the means for clamping;
    introducing the catheter shaft and steerable introducer shaft to a desired location in a subject; and
    engaging a means for advancing the catheter shaft and advancing and measuring a length of the catheter shaft through the introducer positioning device and steerable introducer shaft while the catheter shaft is clamped such that the distal end of the catheter shaft extends past the distal end of the steerable introducer shaft.

* * * * *